Figure 1:
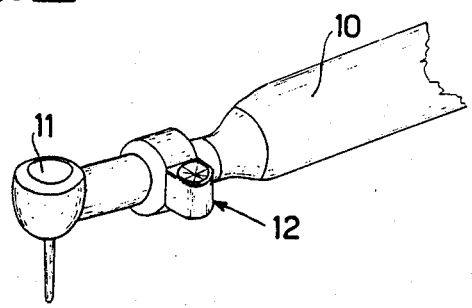

United States Patent [19]

Jaccard

[11] Patent Number: 4,908,949
[45] Date of Patent: Mar. 20, 1990

[54] AIR-BUBBLE LEVEL FOR PORTABLE TOOLS

[75] Inventor: Lé on Jaccard, Curio, Switzerland

[73] Assignee: La Maison Dentaire S.A., Balzers, Liechtenstein

[21] Appl. No.: 257,821

[22] Filed: Oct. 14, 1988

[30] Foreign Application Priority Data

Oct. 14, 1987 [IT] Italy .......................... 22539 B/73[U]

[51] Int. Cl.⁴ ............................................. G01C 9/28
[52] U.S. Cl. ........................................ 33/334; 33/347; 33/390; 33/372
[58] Field of Search .......................... 33/334, 270–273, 33/290, 379, 377, 365, 390, 347, 371, 372

[56] References Cited

U.S. PATENT DOCUMENTS 3,807,051 4/1974 Funakubo .............................. 33/334
4,276,460 6/1981 Haesly .................................. 200/292

FOREIGN PATENT DOCUMENTS 1511490 5/1978 United Kingdom ................. 408/716

Primary Examiner—Harry N. Haroian
Attorney, Agent, or Firm—Foley & Lardner, Schwartz, Jeffery, Schwaab, Mack, Blumenthal & Evans

[57] ABSTRACT

Air-bubble level for portable tools which can be used and operated independently from any changes in position of the tool and which can be easily transferred between tools due to its articulated fastening device.

5 Claims, 3 Drawing Sheets

AIR-BUBBLE LEVEL FOR PORTABLE TOOLS

The present invention relates to an air-bubble level for portable tools.

In the use of portable tools, such as, e.g., drills, cutters, dental handpieces, and so forth, considerable problems arise, if the operator desires to perform a drilling or another operation according to a prefixed axis or direction, because no well-precise references exist, which the operator can use and refer to when performing such an operation.

This happens, e.g., in the dental field when the dentist wishes to intervene on a plurality of adjacent teeth, which have to be capped, once that he has positioned the support pins, fastened, by means of relevant pegs, inside the channels of teeth roots.

In order to give the pin walls their conical shape which is necessary for the positioning of the cap, the greatest attention has to be paid in order that the tools required for such a shaping perimetrically act on the pin with their axis being parallel to the axis of the so-positioned pin.

The above, in order to make easier, once that the above said conical shapings are carried out, the correct positioning of the individual caps, without that problems of mutual interference of the opposite side walls of said caps arise.

In fact, should the two pins of adjacent teeth have such a shape as to define non-parallel axes thereof when the caps are applied, it may happen that the outer walls of said caps force each other, so as to cause, besides well-understandable positioning problems, also a not very much pleasant appearance of the patient's mouth.

In order to make easier such a correct shaping, some handpieces are equipped with an incorporated air-bubble level, which enables the operator to continuously monitor the working position of the same handpiece.

Such an incorporated level does not anyway result convenient, because it only operates properly in precise positions of the handpiece.

In an equivalent way, the same problem occurs, e.g., for an electrical drill incorporating a level in its case.

The purpose of the present invention is to provide an air-bubble level which can be used, and operates, independently from any changes in position of the tool, e.g., in handpiece or drill position, and which can be transferred between tools in an extremely simple way.

These and still further purposes according to the present invention are achieved by providing an air-bubble level for portable tools, characterized in that it comprises a fork-shaped support and a hollow body designed to contain the liquid, having at least one outwards-facing wall portion which is transparent, with said at least one wall portion being always visible with varying operating positions of said portable tool.

Figure 2:
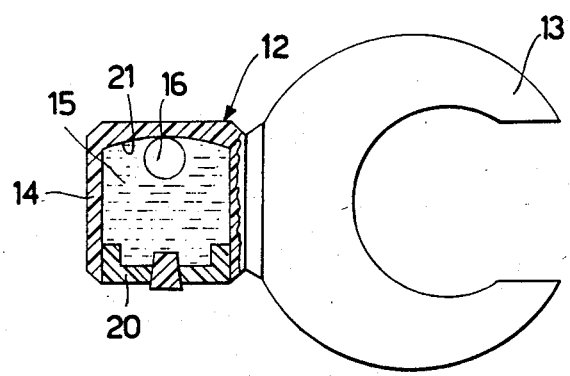
Figure 3:
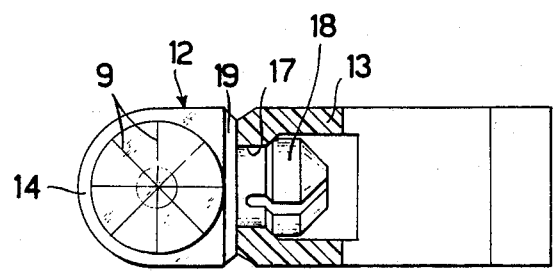
Figure 4:
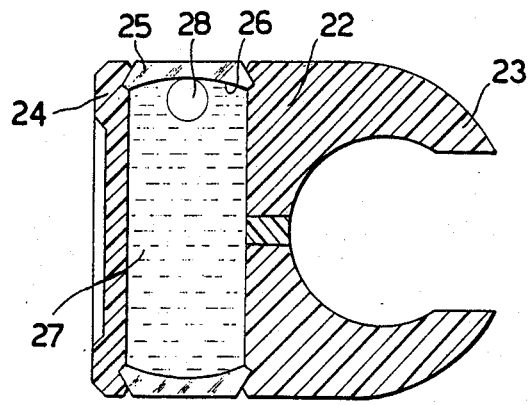
Figure 5:
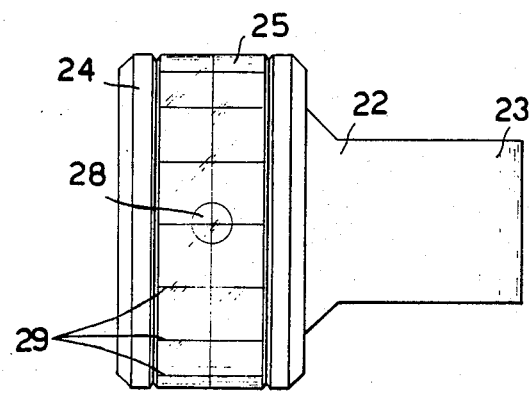
Figure 6:
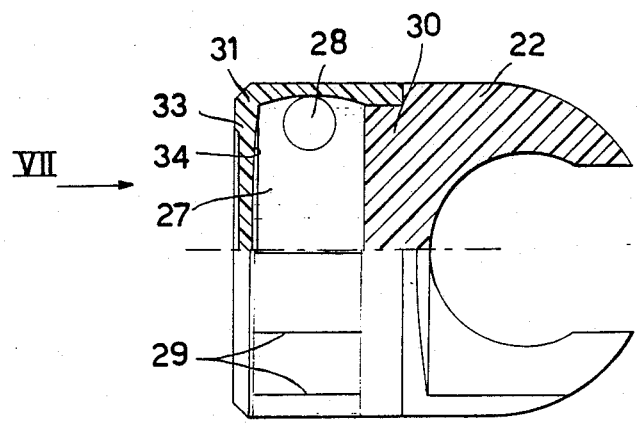
Figure 7:
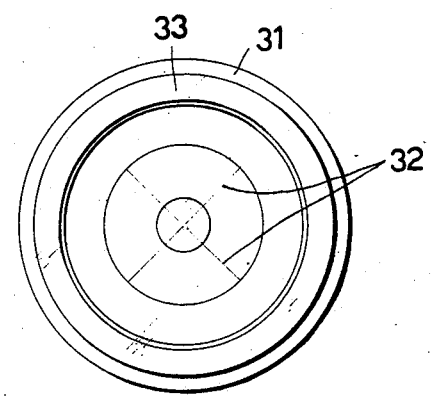

The structural and functional features and the advantages of a bubble-air level according to the present invention are better understood from the following exemplifying, non-limitative disclosure, referred to the hereto attached schematic drawings, wherein:

FIG. 1 shows a perspective view of a level according to the present invention, applied to a dental handpiece, FIG. 2 shows a partially sectional transversal view of a level according to the present invention, FIG. 3 shows a partially sectional top view of the level of FIG. 2, FIG. 4 shows a sectional view of another exemplifying level according to the present invention, FIG. 5 shows a top view of the level of FIG. 4, FIG. 6 shows a partially sectional view of a further level according to the present invention; and FIG. 7 shows a side view according to the arrow VII of FIG. 6.

Referring to FIG. 1, to a portable tool, such as a dental handpiece 10, e.g., equipped with a drill 11, an air-bubble level according to the present invention is applied, which is generally indicated by the reference numeral 12.

As depicted in FIGS. 2 and 3, an air-bubble level 12 comprises a fork-shaped support 13, with which a body 14 designed to contain the liquid 15 and the relevant bubble of air, or of saturated vapour of liquid 16 is rotatably linked.

A bore 17, provided in the centre of the support 13, is suitable for receiving with snap-engagement an elastic expandable appendix 18 which extends from the liquid-containing body 14.

Said liquid-containing body 14 is hollow, and has an essentially cylindrical shape with a flattened side wall 19, to which said appendix 18 is constrained. In its bottom portion, the hollow body 14 is provided with a closure plug element 20, and in its top portion it is provided in its interior with at least one rounded wall portion 21, the bending radius of which has a consistent value, so as to make the level more sensible and precise.

In particular, said wall 21 is transparent, is made as one single piece with said liquid-containing body 14, or is a part of a separate element, which can be made integral with the same liquid-containing body 14, and is provided with reference marks 9, such as graduation marks, e.g., in a radial arrangement, which signal the perfect trueing or correct axial positioning of the body connected to the level 12.

The provision of the coupling consisting of the bore 17 of the support 13, and the expandable appendix 18 makes it possible the position of the body 14 of the level 12 to be varied according to as required by the user, so as to secure that the perfect centering of the air bubble is always visible.

FIGS. 4 and 5 relate to a further exemplifying form of practical embodiment of a level according to the present invention, which is particularly advantageous, in that it does not require any manual adjustments, and is simpler to manufacture.

Said air-bubble level comprises an enbloc body 22, which is provided, at one side, with a fork-shaped support portion 23, and, at the opposite side, with an essentially cylindrical portion 24, which is peripherally grooved with a ring-shaped groove, so as to receive a hollow ring-like element 25 provided with an also annular, continuous, transparent, internally rounded wall portion 26 with a curvature radius of a consistent value. Also inside said ring-like element 25 a liquid 27 and a relevant bubble of air or of saturated vapour 28 are contained.

Therefore, a level with an enbloc body 22 does not require any adjustments, because the correct positioning of the air bubble 28 can be checked in any positions, inasmuch as such a reading is defined by means of the alignments relatively to reference marks 29, such as graduation marks, drawn and provided throughout the 360° of the periphery of the ring-like element 25.

FIGS. 6 and 7 show a further exemplifying form of practical embodiment of a level, similar to the level depicted in FIGS. 4 and 5, wherein form the enbloc body 22 a cylindical portion 30 extends, which is smaller in diameter than the body 22, on which cylindrical portion 30 a body 31, designed to contain the liquid, is constrained, inside which the liquid 27 and the relevant air bubble 28 are contained.

The liquid-containing body 31 has a hollow cylindrical shape open in correspondence of a base thereof, and it is more from a transparent material also provided with reference marks 29, suitable for defining in any positions, always well-visible, and independent from the orientation, the mutual positioning.

Similar reference marks 32 are provided on a base wall 33, which has an inner rounded and curved surface 34 similar to the wall 21 of FIG. 2.

The hereinabove exemplified levels wherein the novel concepts of the present invention are embodied, can be advantageously removed from a handpiece, or from a portable tool, to be applied to another handpiece or portable tool in an extremely simple way, and they furthermore make it possible the reading position to be adapted with varing working positions.

It can be furthermore immediately observed that their structure is extremely simple, and they can be consequently manufactured with a reduced production cost.

I claim:

1. An air-bubble level for portable tools, comprising:
 a body having a fork-shaped resilient support portion and a cylindrical portion, said cylindrical portion having a first base portion attached to said support portion; and
 a transparent ring-shaped member disposed about a circumferential portion of the cylindrical portion, thereby defining a liquid-containing portion therein;
 said transparent, ring-shaped member having a rounded inner surface and being provided with an index for determining the position of an air-bubble in the liquidcontaining portion throughout 360° of the periphery of said transparent, ring-shaped member.

2. The air-bubble level according to claim 1, wherein said cylindrical portion defines a ringshaped groove along a circumferential portion thereof in which said transparent, ring-shaped member is disposed.

3. The air-bubble level according to claim 1, wherein the rounded inner surface of said transparent, ring-shaped member has a constant radius of curvature.

4. The air-bubble level according to claim 1, further comprising:
 a transparent disk-shaped member disposed on a second base portion of the cylindrical portion for viewing the air bubble within said liquid containing portion.

5. The air-bubble level according to claim 4, wherein the transparent disk-shaped member is provided with an index for determining the position of the air bubble.

* * * * *